(12) United States Patent
Zeijlemaker

(10) Patent No.: US 8,818,489 B2
(45) Date of Patent: *Aug. 26, 2014

(54) MEDICAL DEVICE SENSING AND DETECTION DURING MRI

(75) Inventor: Volkert A Zeijlemaker, Landgraaf (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/531,821

(22) Filed: Jun. 25, 2012

(65) Prior Publication Data

US 2012/0265263 A1   Oct. 18, 2012

Related U.S. Application Data

(63) Continuation of application No. 13/238,708, filed on Sep. 21, 2011, now Pat. No. 8,229,543, which is a continuation of application No. 12/712,411, filed on Feb. 25, 2010, now Pat. No. 8,041,410, which is a continuation of application No. 11/278,010, filed on Mar. 30, 2006, now Pat. No. 7,693,568.

(51) Int. Cl.
*A61B 5/05* (2006.01)

(52) U.S. Cl.
USPC .......... 600/411; 600/407; 600/410; 600/16; 600/17; 600/508; 607/9; 607/19

(58) Field of Classification Search
USPC ............... 600/410–423, 16–17, 508–527; 604/9–38, 119–132
See application file for complete search history.

(56) References Cited

U.S. PATENT DOCUMENTS

| 4,091,818 | A | 5/1978 | Brownlee et al. |
| 4,589,420 | A | 5/1986 | Adams et al. |
| 5,629,622 | A | 5/1997 | Scampini |
| 5,694,952 | A | 12/1997 | Lidman et al. |
| 5,697,958 | A | 12/1997 | Paul et al. |
| 5,766,227 | A | 6/1998 | Nappholz et al. |
| 6,188,926 | B1 | 2/2001 | Vock |
| 6,198,972 | B1 | 3/2001 | Hartlaub et al. |
| 6,209,765 | B1 | 4/2001 | Hartlaub et al. |
| 6,501,978 | B2 | 12/2002 | Wagshul et al. |
| 6,647,298 | B2 | 11/2003 | Abrahamson et al. |
| 6,711,442 | B1 | 3/2004 | Swerdlow et al. |
| 6,804,552 | B2 | 10/2004 | Thompson et al. |
| 6,922,580 | B2 | 7/2005 | DeMeester et al. |
| 6,925,328 | B2 | 8/2005 | Foster et al. |
| 7,076,283 | B2 | 7/2006 | Cho et al. |
| 7,231,251 | B2 | 6/2007 | Yonce et al. |
| 7,369,898 | B1 | 5/2008 | Kroll et al. |
| 7,729,770 | B2 * | 6/2010 | Cabelka et al. ............. 607/37 |
| 8,554,318 | B2 * | 10/2013 | Legay ............................. 607/11 |
| 2001/0016782 | A1 | 8/2001 | McKinnon et al. |
| 2002/0128689 | A1 | 9/2002 | Connelly et al. |

(Continued)

FOREIGN PATENT DOCUMENTS

| EP | 0713714 | 5/1996 |
| WO | 03037429 | 5/2003 |
| WO | 2005035048 | 4/2005 |

*Primary Examiner* — James Kish
(74) *Attorney, Agent, or Firm* — Michael J. Ostrom; Stephen W. Bauer

(57) ABSTRACT

A medical device includes a sensor for sensing for an MRI gradient magnetic field and a microprocessor configured to operate in a signal processing mode in which electrical signals induced by the gradient magnetic field are not counted as cardiac events.

16 Claims, 6 Drawing Sheets

(56) References Cited

U.S. PATENT DOCUMENTS

| | | |
|---|---|---|
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144718 A1 | 7/2003 | Zeijlemaker |
| 2003/0144719 A1 | 7/2003 | Zeijlemaker |
| 2003/0144721 A1 | 7/2003 | Villaseca et al. |
| 2004/0015197 A1 | 1/2004 | Gunderson |
| 2004/0088012 A1 | 5/2004 | Kroll et al. |
| 2005/0070787 A1 | 3/2005 | Zeijlemaker |
| 2006/0173369 A1 | 8/2006 | Kaski |
| 2007/0132581 A1 | 6/2007 | Molyneaux et al. |
| 2007/0255332 A1* | 11/2007 | Cabelka et al. ............ 607/37 |

\* cited by examiner

MEDICAL DEVICE SENSING AND DETECTION DURING MRI

This application is a continuation of U.S. application Ser. No. 13/238,708, filed Sep. 21, 2011, which is a continuation application of U.S. application Ser. No. 12/712,411, filed Feb. 25, 2010 and granted as U.S. Pat. No. 8,014,410, which is a continuation of Ser. No. 11/278,010, filed Mar. 30, 2006 and granted as U.S. Pat. No. 7,693,568. Each of the above referenced applications and patents are incorporated herein by reference in their entirety.

TECHNICAL FIELD

The present invention relates to medical systems and devices and more particularly to sensing and detection performed by these devices during magnetic resonance imaging (MRI).

BACKGROUND

The technology explosion in the medical device industry has resulted in a variety of innovative diagnostic and therapeutic devices and methods. Many medical devices, for example, including electrocardiographic monitors, pacemakers, cardioverter-defibrillators and neural stimulators, are operatively coupled to electrodes, which are joined to elongate lead wires that extend from the devices to a target site either on or within a body of a patient. The electrodes sense electrical signals from the patient, for example cardiac depolarization signals, which are used to diagnose the patient and, in many cases, may be used to guide or dictate therapy delivery. Having such a device may be a contraindication for MRI, due, at least in part, to MRI gradient magnetic fields and radio-frequency (RF) energy, which can induce electrical signals in the lead wires; the MRI artifact can obfuscate cardiac depolarization induced signals leading to erroneous cardiac event detection which can compromise therapy delivery during MRI.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention.

Figure 1:
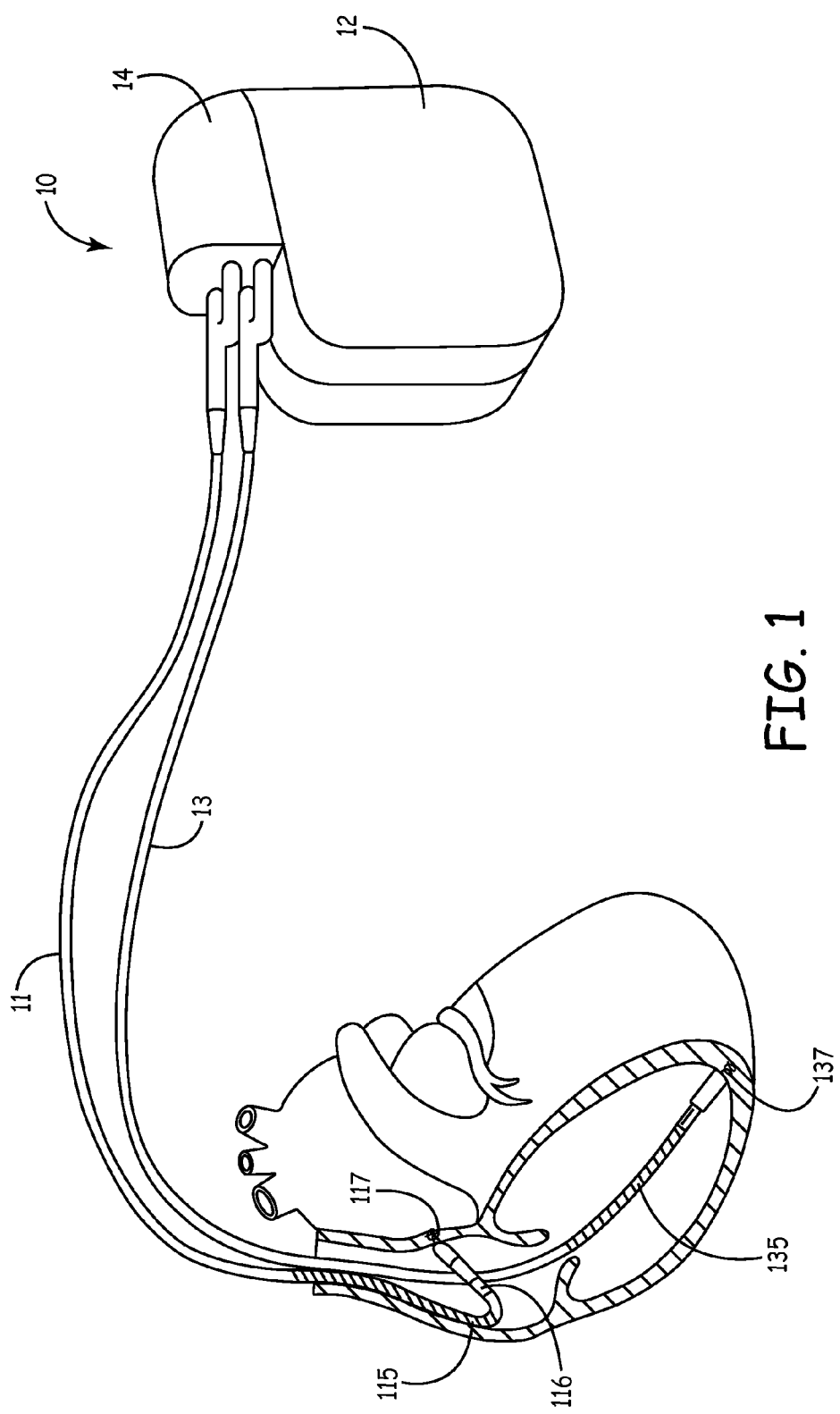
FIG. 1 is a schematic of an exemplary medical system according to some embodiments of the present invention.

FIG. 1 is a schematic of an exemplary medical system according to some embodiments of the present invention. FIG. 1 illustrates the system including a device 10 to which a right atrial medical electrical lead 11 and a right ventricular medical electrical lead 13 are operatively coupled via a connector module 14. Lead 11 is shown including a defibrillation electrode 115, a first pace/sense electrode 116 and a second pace/sense electrode 117, which is contacting tissue of a right atrial appendage. Lead 13 is shown including a defibrillation electrode 135 and a pace/sense electrode 137 fixed to tissue in a right ventricular apex. According to the illustrated embodiment, device 10 includes a can or housing 12, which serves as another defibrillation electrode to act in concert with electrodes 115 and 135; such an electrode is known to those skilled in the art as an 'active can'. The system shown in FIG. 1, well known to those skilled in the art, is configured for cardiac pacing, sensing and defibrillation. According to embodiments of the present invention, the system further includes a capacity to detect an MRI gradient magnetic field and respond to the detected field, such that electrical signals induced in either one or both of leads 11, 13, by the gradient magnetic field and a subsequent MRI RF pulse are not inadvertently counted as cardiac events by the device.

Figure 2:
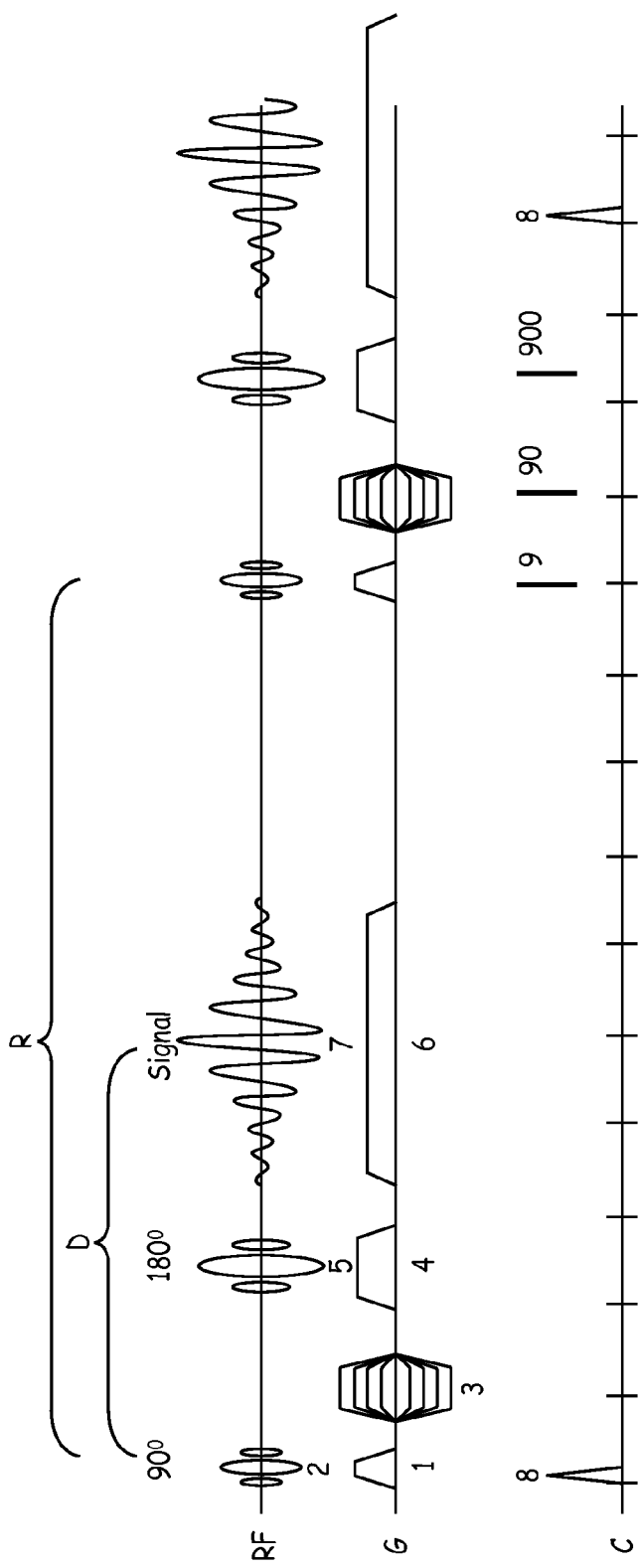
FIG. 2 is a collection of exemplary plots representing artifact-inducing MRI activity and cardiac electrical activity.
Figure 3:
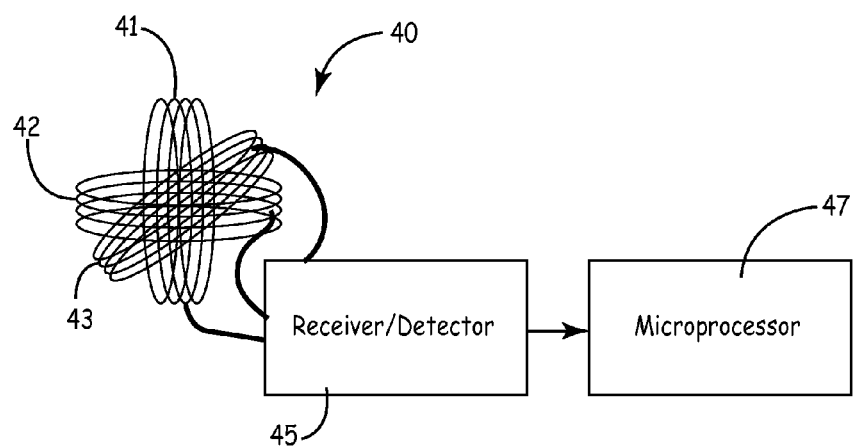
FIG. 3 is a schematic of a transducer according to some embodiments of the present invention.

FIG. 2 is a collection of exemplary plots representing artifact-inducing MRI activity and cardiac electrical activity. Those skilled in the art understand that, in order for RF pulses to produce a signal for MRI imaging, a magnetic field must be altered on a local level coinciding with a location at which the image is desired. Plots RF and G of FIG. 3 represent a sequence of MRI induced RF pulses and associated gradient magnetic fields, respectively; those skilled in the art will recognize slice select gradients 1 and 4 associated with a 90° RF pulse 2 and a 180° RF pulse 5, respectively, and a phase encoding gradient 3, for first phase encoding, and a read out gradient 6 activated while signal 7 is sampled. If a lead wire, for example one included in lead 13 of FIG. 1, is coincident with the location at which the image is being generated, the wire will pick up electrical artifacts generated by the gradient fields and RF pulses. Since a magnitude of a RF pulse artifact is typically greater than 3 volts whereas cardiac electrical activity is on the order of millivolts, the RF artifact can be erroneously detected as a cardiac event, i.e. ventricular depolarization, and can completely 'drown out' or mask signals of actual cardiac events.

In order to demonstrate interference of the MRI activity, FIG. 2 further shows, under the RF and G plots, a third plot C representing normal cardiac electrical activity in terms of ventricular depolarization, or R-waves 8, for example sensed by electrodes 137 and 135 of FIG. 1. A time scale for each plot of FIG. 2 is 50 milliseconds per hash mark shown along plot C, but plots RF and G may shift with respect to the electrical activity shown on plot C depending on when the MRI activity is initiated within the cardiac cycle, represented by the interval between R-waves 8. Those skilled in the art will appreciate that a timing of RF and G events can vary. For example, each sequence of magnetic gradient fields and RF pulses may have a duration D between approximately 5 and 250 milliseconds and a time between sequences R may be between approximately 100 and 3,000 milliseconds; furthermore, a normal interval between R-waves 8, or an R-R interval, may be between approximately 600 and 1200 milliseconds. FIG. 2 illustrates D at approximately 250 milliseconds, R at approximately 500 milliseconds, and the R-R interval, along plot C, at approximately 700 milliseconds. With reference to FIG. 2, if plot C represents paced cardiac activity, for example, for a bradycardia patient, the RF pulse coincident with a marker 9, shown along plot C, may be detected as an intrinsic R-wave causing a device, i.e. device 10, to withhold the second pacing pulse shown at the far right hand side of plot C. It will be appreciated that if the plots RF and G shift in time with respect to the plot C, the RF pulse will coincide with either markers 90 or 900 to be detected as a cardiac event. Thus, it can be seen that RF pulse timing coinciding with normal to slower rhythms, i.e. in the range of 600 to 1200 milliseconds, may cause device 10 to withhold pacing therapy when it may be needed. Alternately, RF pulse timing in the range of 100 to 600 milliseconds coincides with dangerously fast rhythms, for example ventricular tachyarrhythmia (VT) and ventricular fibrillation (VF), and can cause device 10 to falsely detect VT or VF and thus deliver unneeded pacing and/or high voltage therapy delivery.

Figure 4:
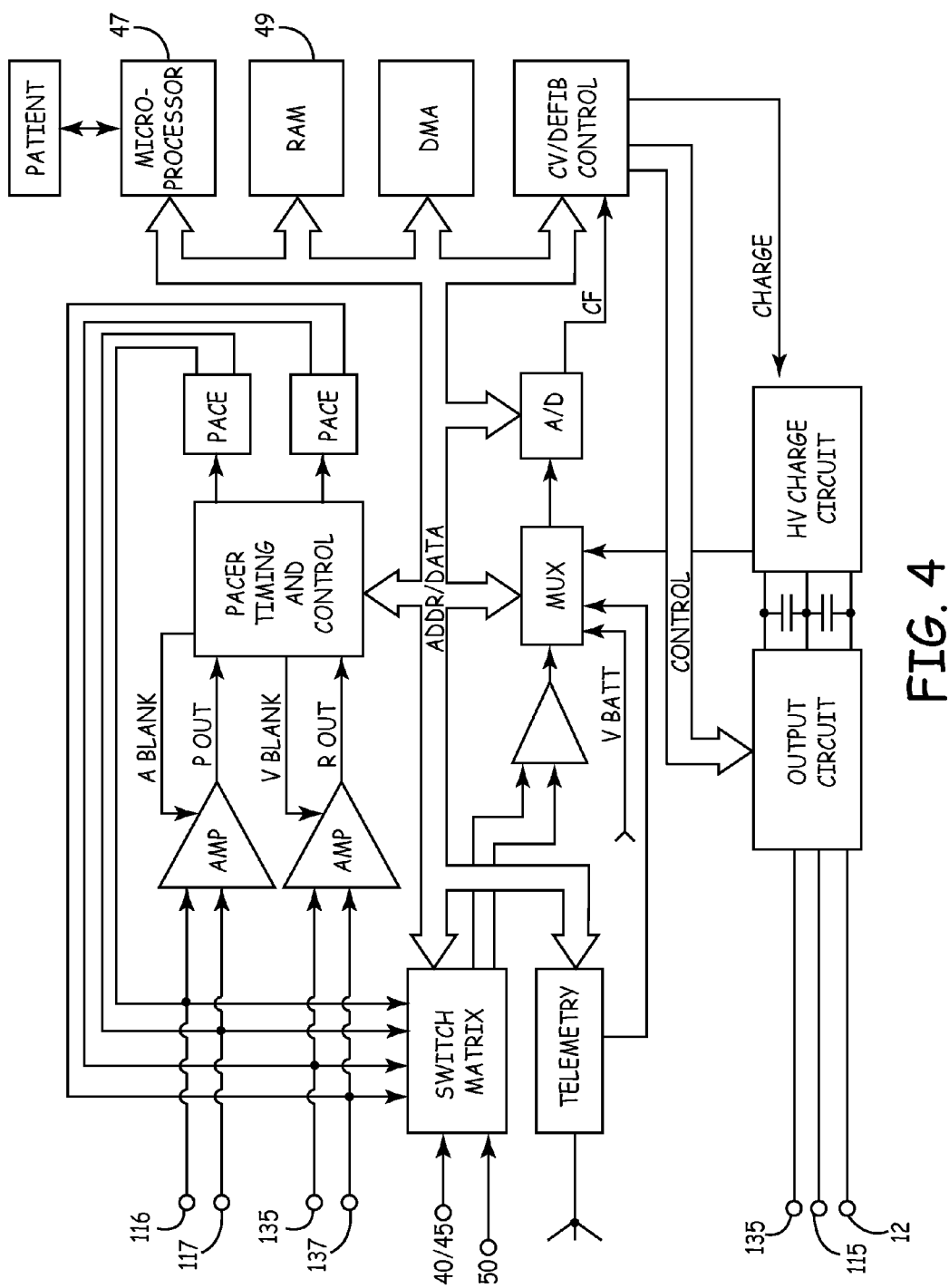
FIG. 4 is a functional block diagram corresponding to the system of FIG. 1.

FIG. 3 is a schematic of a transducer 40, according to some embodiments of the present invention, which can detect an MRI gradient magnetic field via inductive coupling of the field with one of three orthogonal coils 41, 42, 43, depending upon the orientation of the field. FIG. 3 illustrates each coil 41, 42, 43 coupled to a receiver/detector 45 which provides input into a microprocessor 47 which causes a signal processing mode of device 10 to be altered to account for MRI artifact. Coils 41, 42, 43 are sensitive enough to detect small changes in the magnetic field, for example, between approximately 5 Tesla per second and approximately 300 Tesla per second, and receiver/detector 45 may include a programmable detection threshold. According to some embodiments of the present invention, transducer 40, receiver/detector 45 and microprocessor 47 are contained within housing 12 of device 10 along with other electronic components of device 10. FIG. 4 is a functional block diagram corresponding to the system of FIG. 1, which illustrates an exemplary microprocessor controlled system architecture, known to those skilled in the art, into which transducer 40 and receiver 45 are integrated. It should be noted that other embodiments of the present invention may be practiced with other types of system architecture known to those skilled in the art, such as those employing dedicated digital circuitry.

Figure 5A:
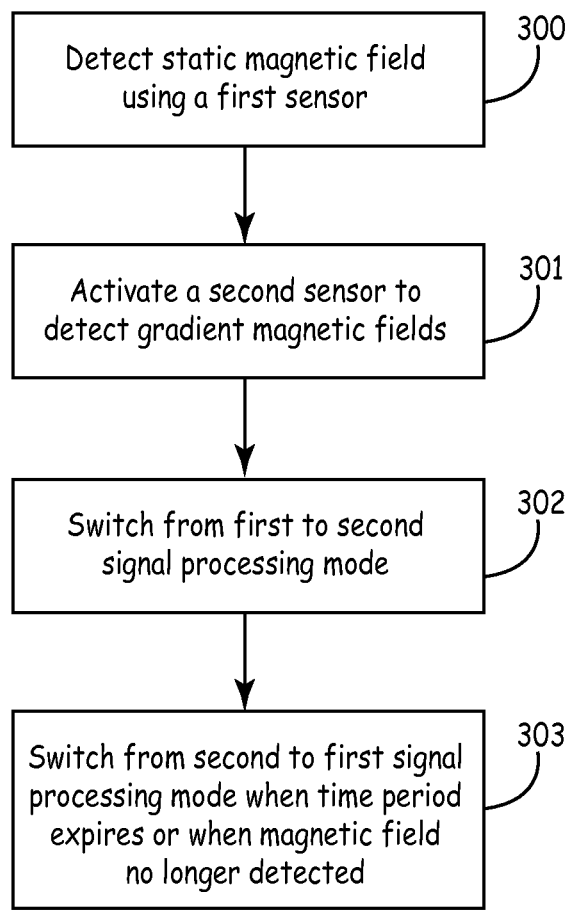
FIG. 5A is a flow chart outlining methods according to some embodiments of the present invention.

FIG. 5A is a flow diagram outlining methods according to some embodiments of the present invention. Methods of the present invention may be stored as programs, or algorithms, on a computer readable medium in a memory of device 10, for example, a read only memory (ROM) of microprocessor 45 (FIG. 4). FIG. 5A illustrates a process in which MRI magnetic fields are detected. According to embodiments of the present invention, the magnetic fields are gradient magnetic fields, for example detected by transducer 40 of FIG. 3. According to some methods, the magnetic fields also include the relatively large static magnetic field associated with MRI, for example, greater than 0.1 Tesla (typically in a range from 0.5 Tesla to 2 Tesla); such a field may be detected at step 300 by a Hall effect sensor 50 (FIG. 4), embodiments of which are known to those skilled in the art. Once such a sensor detects the static field, transducer 40 may be activated to detect the gradient fields at step 301. According to other embodiments, a reed switch may activate transducer 40 in the presence of the relatively large static magnetic field. According to a second step 302, a signal indicating the presence of a gradient field, for example, from transducer 40, causes device 10 to switch from a first signal processing mode to a second signal processing mode capable of discounting MRI artifact. At step 303, after a predetermined time, for example, covering a full length of an MRI procedure, or once gradient fields are no longer detected for a predetermined time period, or once the static magnetic field is no longer detected, device 10 is caused to switch back to the first signal processing mode.

According to some methods of the present invention, the second signal processing mode, of step 302, includes an introduction of a blanking period as a mechanism for discounting MRI artifact. In such a method, a blanking period is introduced in response to gradient magnetic field detection so that signals induced in leads 11, 13 by the gradient magnetic fields and subsequent RF bursts are ignored during the period of imaging activity or scanning. The blanking period may be predetermined and preprogrammed into device 10 according to the scanning period of a particular MRI machine employed, or may be dynamically controlled by input corresponding to detection of the gradient magnetic field, for example, from transducer 40. A blanking time period may be programmed to be between approximately 10 milliseconds and approximately 150 milliseconds. According to the example illustrated in FIG. 2, wherein D is approximately 250 milliseconds, it will be appreciated that a blanking period of approximately 150 milliseconds starting at detection of gradient field 1 will encompass both RF pulses 2, 5.

Figure 5B:
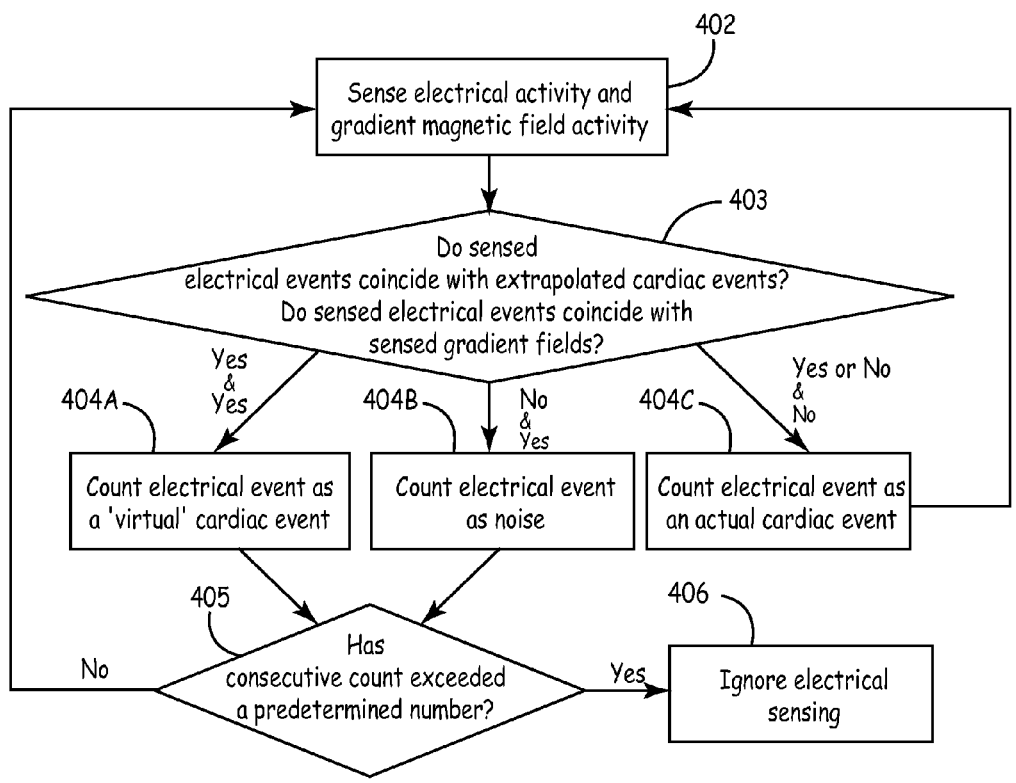
FIG. 5B is a flow diagram outlining a signal processing algorithm according to one embodiment of the present invention.

FIG. 5B illustrates another method of the present invention. FIG. 5B is a flow diagram outlining a signal processing algorithm, for the second signal processing mode of step 302, for discounting MRI artifact. In this method, a history of cardiac event timing for a particular patient is stored in device 10, for example, in a random access memory (RAM) 49 (FIG. 4), and used to extrapolate a series of the cardiac events for use during MRI interference. When electrical activity and gradient field activity are sensed, per step 402, a decision is made at step 403 based upon the timing of the sensed electrical events. If electrical events, for example sensed by electrodes of either lead 11 or 13 of FIG. 1, do not coincide with gradient field activity, for example sensed by transducer 40 of FIG. 3, whether or not the electrical events coincide with extrapolated cardiac events, the events are counted as an actual cardiac event at step 404C. (This decision of course is tempered by additional state of the art signal conditioning that accounts for other types of over-sensing.) If sensed electrical events do coincide with the sensed gradient fields but not with extrapolated cardiac events, the events are counted as noise at step 404B. If sensed electrical events coincide with both of the extrapolated cardiac events and the sensed gradient fields, the events are counted as 'virtual' or potential cardiac events at step 404A. The 'virtual' events are processed by device 10, according to typical state of the art limitations for such devices, for control of therapy delivery to maintain physiological cardiac function. Counters of these events are included in microprocessor 47 and/or RAM 49 of the architecture depicted in FIG. 4. Per step 405, when a consecutive count of noise events and 'virtual' cardiac events exceeds a predetermined number, electrical sensing is ignored at step 406. If electrical sensing is ignored, then device 10 may switch into a prescribed mode of therapy delivery, for example pacing stimulation at a prescribed number of beats per minute.

According to some other methods of the present invention, the second signal processing mode, of step 302, introduces modified signal conditioning, i.e. attenuation and/or filtering, to reduce MRI artifact so that cardiac electrical activity is detectable. According to one method of this type, the second mode includes attenuation of RF frequency (approximately 6-300 MHz) induced signals received through the lead wire, preferably to a level below a ventricular depolarization, or R-wave, amplitude, which is typical of the patient having device 10. According to other methods of this type, the second mode either includes filtering that rejects gradient field frequency (approximately 1-50 kHz) induced signals received through the lead wire, or imposing a sensitivity threshold exceeding a maximum amplitude of gradient field induced signals received through the lead wire, which are typically of a lower amplitude than ventricular depolarization, or R-wave, amplitudes.

In the foregoing detailed description, the invention has been described with reference to specific embodiments. However, it may be appreciated that various modifications and changes can be made without departing from the scope of the invention as set forth in the appended claims. For example, although embodiments have been described in the context of cardiac pacing and defibrillation, embodiments of the present invention include any type of medical device that includes leads for sensing electrical activity of any part of a body.

The invention claimed is:

1. An implantable medical device comprising:
   a first sensor configured to detect the presence of a static magnetic field;
   a second sensor, separate from the first sensor, configured to detect the presence of gradient magnetic fields, wherein the second sensor is activated only after the first sensor detects the presence of the static magnetic field; and
   a microprocessor configured to switch operation of the implantable medical device from a first signal processing mode to a second signal processing mode in response to detecting the presence of gradient magnetic fields.

2. The implantable medical device of claim 1, wherein the first sensor comprises one of a Hall effect sensor and a reed switch.

3. The implantable medical device of claim 2, wherein the second sensor comprises a transducer that includes three orthogonal coils configured to detect the gradient magnetic fields.

4. The implantable medical device of claim 1, wherein the second sensor comprises a transducer that includes three orthogonal coils configured to detect the gradient magnetic fields.

5. The implantable medical device of claim 1, wherein the microprocessor switches operation of the implantable medical device from the second operation mode to the first operating mode after a predetermined time or no longer detecting the static magnetic field.

6. The implantable medical device of claim 1, wherein the microprocessor is configured to introduce a blanking period in response to detecting the gradient magnetic fields while operating in the second signal processing mode.

7. The implantable medical device of claim 6, wherein the blanking period is preprogrammed into the implantable medical device according to the scanning period of a particular MRI machine employed.

8. The implantable medical device of claim 6, wherein the blanking period is dynamically controlled by input corresponding to detection of the gradient magnetic field.

9. The implantable medical device of claim 1, wherein the microprocessor switches operation of the implantable medical device from the second operation mode to the first operating mode after no longer detecting gradient magnetic fields for a predetermined time period.

10. A method comprising:
    detecting the presence of a static magnetic field with a first sensor of an implantable medical device;
    activating a second sensor of the implantable medical device, separate from the first sensor, only after detecting the presence of the static magnetic field;
    detecting the presence of gradient magnetic fields with the second sensor; and
    configuring operation of the implantable medical device from a first signal processing mode to a second signal processing mode in response to detecting the presence of gradient magnetic fields.

11. The method of claim 10, further comprising configuring operation of the implantable medical device from the second operation mode to the first operating mode after a predetermined time.

12. The method of claim 10, further comprising configuring operation of the implantable medical device from the second operation mode to the first operating mode upon no longer detecting gradient magnetic fields for a predetermined time period.

13. The method of claim 10, further comprising configuring operation of the implantable medical device from the second operation mode to the first operating mode upon no longer detecting the static magnetic field.

14. The method of claim 10, further comprising introducing a blanking period in response to detecting the gradient magnetic fields while operating in the second signal processing mode.

15. The method of claim 14, further comprising preprogramming the blanking period according to the scanning period of a particular MRI machine employed.

16. The method of claim 14, further comprising dynamically controlling the blanking period by input corresponding to detection of the gradient magnetic fields.

* * * * *